US007479481B2

(12) United States Patent
Molina

(10) Patent No.: US 7,479,481 B2
(45) Date of Patent: Jan. 20, 2009

(54) TREATMENT OF OCULAR DISEASES AND DISORDERS USING LANTIBIOTIC COMPOSITIONS

(75) Inventor: Luis Molina, Durham, NC (US)

(73) Assignee: Molichem Medicines, Inc., Chapel Hill, NC (US)

(*) Notice: Subject to any disclaimer, the term of this patent is extended or adjusted under 35 U.S.C. 154(b) by 169 days.

(21) Appl. No.: 11/123,436

(22) Filed: May 6, 2005

(65) Prior Publication Data

US 2005/0250681 A1 Nov. 10, 2005

Related U.S. Application Data

(60) Provisional application No. 60/569,501, filed on May 6, 2004.

(51) Int. Cl.
*A61K 38/00* (2006.01)
*A61K 9/14* (2006.01)
*C07K 16/00* (2006.01)

(52) U.S. Cl. .................. 514/9; 514/912; 514/913; 530/317; 424/45; 424/46

(58) Field of Classification Search .................. 514/9, 514/912, 913; 530/317; 424/45, 46
See application file for complete search history.

(56) References Cited

U.S. PATENT DOCUMENTS

| | | | |
|---|---|---|---|
| 4,209,505 A | 6/1980 | Mikhail | |
| 5,137,728 A | 8/1992 | Bawa | |
| 5,512,269 A | 4/1996 | Molina y Vedia et al. | |
| 5,641,781 A | 6/1997 | Cuberes-Altisent et al. | |
| 5,651,957 A | 7/1997 | Molina y Vedia et al. | |
| 5,683,675 A | 11/1997 | Molina y Vedia et al. | |
| 5,716,931 A | 2/1998 | Molina y Vedia et al. | |
| 5,849,706 A | 12/1998 | Molina y Vedia et al. | |
| 5,900,407 A | 5/1999 | Yerxa et al. | |
| 5,968,913 A | 10/1999 | LaCroix et al. | |
| 5,972,988 A | 10/1999 | Macias | |
| 5,981,473 A | 11/1999 | Barefoot et al. | |
| 6,027,715 A | 2/2000 | Poznelo | |
| 6,043,219 A | 3/2000 | Iandolo et al. | |
| 6,136,794 A | 10/2000 | Cook et al. | |
| 6,159,952 A | 12/2000 | Shaffer et al. | |
| 6,200,551 B1 | 3/2001 | Morgan | |
| 6,221,357 B1 | 4/2001 | Bok et al. | |
| 6,268,380 B1 | 7/2001 | Tjoeng et al. | |
| 6,277,855 B1 | 8/2001 | Yerxa | |
| 6,291,469 B1 | 9/2001 | Fisher et al. | |
| 6,315,996 B1 | 11/2001 | O'Callaghan | |
| 6,319,908 B1 | 11/2001 | Yerxa et al. | |
| 6,331,529 B1 | 12/2001 | Yerxa et al. | |
| 6,348,589 B1 | 2/2002 | Pendergast et al. | |
| 6,387,886 B1 | 5/2002 | Montgomery et al. | |
| 6,420,347 B1 | 7/2002 | Jacobus et al. | |
| 6,423,694 B1 | 7/2002 | Drutz et al. | |
| 6,423,721 B1 | 7/2002 | Harris et al. | |
| 6,444,695 B1 | 9/2002 | Mahajan et al. | |
| 6,448,276 B1 | 9/2002 | Yerxa | |
| 6,451,288 B1 | 9/2002 | Boucher et al. | |
| 6,462,028 B2 | 10/2002 | Pendergast et al. | |
| 6,489,335 B2 | 12/2002 | Peyman | |
| 6,548,658 B2 | 4/2003 | Yerxa | |
| 6,565,861 B1 | 5/2003 | Tiffany et al. | |
| 6,569,903 B2 | 5/2003 | Honma et al. | |
| 6,596,725 B2 | 7/2003 | Peterson et al. | |
| 6,656,920 B2 | 12/2003 | Fox et al. | |
| 6,673,779 B2 | 1/2004 | Jacobus et al. | |
| 6,693,109 B2 | 2/2004 | Fisher et al. | |
| 6,713,458 B1 | 3/2004 | Yerxa et al. | |
| 6,716,813 B2 | 4/2004 | Lim et al. | |
| 2004/0033955 A1 | 2/2004 | Catania et al. | |
| 2005/0506282 | 11/2005 | Molina | |

FOREIGN PATENT DOCUMENTS

| | | |
|---|---|---|
| JP | 2002-053492 A2 | 2/2002 |
| WO | WO 94/28726 A2 | 12/1994 |
| WO | WO 98/34593 A1 | 8/1998 |
| WO | WO 99/0998 A1 | 3/1999 |
| WO | WO 01/80844 A2 | 11/2001 |
| WO | WO 01/87288 A2 | 11/2001 |
| WO | WO 01/87913 A2 | 11/2001 |
| WO | WO 02/09702 A2 | 2/2002 |
| WO | WO 02/16381 A2 | 2/2002 |
| WO | WO 2004/037167 | 5/2004 |

OTHER PUBLICATIONS

Burrage, S., et al., "Biomimetic synthesis of lantibiotics," *Chem. Eur. J.*, 6(8):1455-1466 (Apr. 14, 2000).

(Continued)

*Primary Examiner*—Jon Weber
*Assistant Examiner*—Abdel A Mohamed
(74) *Attorney, Agent, or Firm*—King & Spalding

(57) ABSTRACT

Compositions and methods for treating ocular diseases and disorders are provided. The composition can contain at least one lantibiotic, which can be administered topically by injection, systemically, or by other appropriate means. The methods provided include the administration of a therapeutically effective amount of a formulation containing at least one lantibiotic to the appropriate section of the eye.

10 Claims, No Drawings

OTHER PUBLICATIONS

International Search Report, PCT/US05/15821, Mar. 20, 2006, p. 2.

Monnet, D., et al., "Ophthalmic findings and frequency of extraocular manifestations in patients with HLA-B27 uveitis: a study of 175 cases," *Ophthalmology*, 111(4):802-809 (Apr. 2004).

O'Neil, M.J., et al., Eds., *The Merck Index*, 13th ed. (Merck & Co., Inc., Whitehouse Station, NJ, 2001), p. 480, No. 2780, "Cycloserine".

Pag, U., and Sahl, H.-G., "Multiple activities in lantibiotics—models for the design of novel antibiotics?" *Curr. Pharm. Des.*, 8(9):815-833 (2002).

Boschelli, D.H., et al., "Inhibition of E-selectin-, ICAM-1-, and VCAM-1-, and VCAM-1-mediated cell adhesion by benzo[b]thiophene-, benzofuran-, indole-, and naphthalene-2-carboxamides: identification of PD 144795 as an antiinflammatory agent," *J. Med. Chem.*, 38 (22):4597-4614 (Oct. 27, 1995).

Boucher, R., et al., "Mechanisms and therapeutic actions of uridine triphosphates in the lungs," *Adenosine and Adenine Nucleotides: From Molecular Biology to Integrative Physiology*, (L. Belardelli, et al., Eds., Alumwer Academic Publishers, Boston, 1995), pp. 525-532.

Bowie, E.M., et al., "Corticosteroids, central serous chorioretinopathy, and neurocysticercosis," *Arch. Ophthalmol.*, 122(2):281-283 (Feb. 2004).

Brewitt, H., et al., "Dry Eye Disease: The Scale of the Problem." *Surv. Ophthalmol.* 45 Suppl. 2:S199-S202 Mar. 2001).

Chang, Y.H., et al., *Eur. J. Pharmacol.*, 69(2):155-164 (Jan. 16, 1981). Effects of pharmacologic agents on the reversed passive Arthus reaction in the rat.

Cloutier, M.M., et al., "Duramycin enhances chloride channel activity in cystic fibrosis nasal epithelial cells." *Pediatric Pulmonology*, 2(Supplement):99 (Abstract 15) (1988).

Cloutier, M.M., et al., "Duramycin enhances chloride secretion in airway epithelium." *Am J Physiol.—Cell Physiol.*, Sep;259(3 Pt 1):C450-C454 (Sep. 1990).

De Nijs, E., et al., "The adverse effects of corticosteroids in central serous chorioretinopathy" *Bull. Soc. Belge Ophtalmol.*, 289:35-41 (2003).

Diamond, M.S., et al., "The dynamic regulation of integrin adhesiveness" *Current Biology*, 4(6):506-517 (Jun. 1, 1994).

Forrest, J.B., et al., "Activation of nasal cilia in immotile cilia syndrome," *Am. Rev. Respir. Dis.*, 120(3):511-515 (Sep. 1979).

Foulks, G.N., "The evolving treatment of dry eye," *Ophthalmol. Clin. North Am.*, 16(1):29-35 (Mar. 2003).

Friedlander, A.H., et al., "Late-life depression: psychopathology, medical interventions, and dental implications," *Oral Surg. Oral Med. Oral Pathol. Oral radiol. Endod.*, 94(4):404-412 (Oct. 2002).

Gross, E., et al., "Subtilin, VI: Die Struktur des Subtilins," *Z. Physiol. Chem.*, 354:810-812 (Jul. 1973).

Hayashi, F., et al., "The structure of PA48009: The revised structure of duramycin," *J. Antibiotics* (Tokyo), LXIII(11):1421-1430 (Nov. 1990).

Hechard, Y., et al., "Mode of action of modified and unmodified bacteriocins from Gram-positive bacteria," *Biochimie*, 84(5-6):545-557 (May-Jun. 2002).

Kellerman, D.J., "$P2Y_2$ Receptor agonists: a new class of medication targeted at improved mucociliary clearance," *Chest*, 121(5 Suppl.): 201S-205S (May 2002).

Kellner, R., et al, "Gallidermin: a new lanthionine-containing polypeptide antibiotic," *Eur. J. Biochem.* 177(1), 53-59 (Oct. 15, 1988).

Kessler, H., et al., "204. The structure of the polycylic nonadecapeptide *Ro 09-0198*," *Helv. Chim. Acta*, 71:1924-1929 (1988).

Kettenring, J.K., et al., "Sequence determination of actagardine, a novel lantibiotic, by homonuclear 2D NMR spectroscopy," *J. Antibiotics*, XLIII(9):1082-1088 (Sep. 1990).

Kishimoto, T.K., et al., "Integrins, ICAMs, and selectins: role and regulation of adhesion molecules in neutrophil recruitment to inflammatory sites," *Adv. Pharmacol.*, 25:117-169 (1994).

Knowles, M.R., et al., "Activation by extracellular nucleotides of chloride secretion in the airway epithelia of patients with cystic fibrosis," *N. Eng. J. Med.*, 325(8):533-538 (Aug. 22, 1991).

Lansley, A.B., et al., "Control of the beat cycle of respiratory tract cilia by Ca2= and cAMP.," *Am. J. Physiol.*, 263(2 Pt. 1):L232-L242 (Aug. 1992).

Lethem, M.L., et al., "Nucleotide regulation of goblet cells in human airway epithelial explants: normal exocytosis in cystic fibrosis," *Am. J. Respir. Cell. Mol. Biol.*, 9(3):315-322 (Sep. 1993).

McNulty, M.J., et al., "Pharmacokinetics and tissue distribution of the nonadecapeptide Moli1901 in rats and mice," *Xenobiotica*, Feb;33(2):197-210 (Feb. 2003).

Monnet, D., et al., "Ophthalmic findings and frequency of extraocular manifestations in patients with HLA-B27 uveitis: a study of 175 cases,," *Ophthalmology*, 111(4):802-809 (Apr. 2004).

Musza, L.L., et al., "Potent new cell adhesion inhibitors from the root of *trichilia rubra*," *Tetrahedron*, 50(39):11369-11378 (1994).

Nakamura, S., et al., "Inhibitory effect of duramycin on partial reactions catalyzed by (Na=,K=)-adenosinetriphosphatase from dog kidney," *Biochem.*, 23(2):385-389 (Jan. 17, 1984).

Nussenblatt, R.B., et al., "Cyclosporine: immunology, pharmacology and therapeutic uses," *Survey of Ophthalmology*, 31(3):159-169 (Nov.-Dec. 1986).

O'Neil, M.J., Sr. Ed., et al., *The Merck Index: An Encyclopedia of Chemicals, Drugs, and Biologicals*, 13th Ed., O'Neil, M.J. Sr. Ed. (Merck & Co., Inc., Whitehouse Station, New Jersey, 2001), entry No. 2781 ("Cyclosporin A"), p. 480.

Pedersen, M.., "Ciliary Activity and pollution," *Lung*, 168 Suppl. :368-376 (1990).

Pridham, T.G., et al., "Antibiotics against plant disease. II. Effective agents produced by streptomyces cinnamomeus forma azacoluta F. Nov.," *Phytopathology*, 46:575-581 (Oct. 1956).

Roberts, M., et al., "Stimulation of sodium transport by duramycin in cultured human colonic epithelia," *J. Pharmacol. Exp. Ther.*, 259(3):1050-1058 (Dec. 1991).

Sahl, H.-G., "Influence of the staphylococcinlike peptide Pep 5 on membrane potential of bacterial cells and cytoplasmic membrane vesicles," *J. Bacteriol.*, 162(2):833-836 (May 1985).

Sanfilippo, P.J., et al., "Novel thiazole based heterocycles as inhibitors of LFA-1/ICAM-1 mediated cell adhesion," *J. Med. Chem.*, 38(7):1057-1059 (Mar. 21, 1995).

Schalenbourg, A., et al., "Corticosteroid-induced central serous chorioretinopathy in patients with ocular inflammatory disorders," *Klinische Monatsblätter für Augenheilkunde*, 219(4):264-267 (Apr. 2002).

Schnell, N., et al., "Prepeptide sequence of epidermin, a ribosomally synthesized antibiotic with four sulphide-rings," *Nature*, 333(6170):276-278 (May 19, 1988).

Shotwell, O.L., et al., "Antibiotics against plant disease. III. Duramycin, a new antibiotic from *IStreptomyces cinnaomoeus* forma *azacoluta*," *J. Am. Chem. Soc.* 80:3912-3915 (Aug. 5, 1958).

Springer, T.A., "Adhesion receptors of the immune system.," *Nature*, 346(6283):425-434 (Aug. 2, 1990).

Wakamiya, T., et al., "The structure of ancovenin, a new peptide inhibitor of Angiotensin I Converting Enzyme," *Tetrahedron Lett,.* 26(5):665-668 (1985).

Wandel, T., et al., "Glaucoma treatment with once-daily levobunolol," *Amer. J. Ophthalmol.*, 101(3):298-304 (Mar. 15, 1986).

TREATMENT OF OCULAR DISEASES AND DISORDERS USING LANTIBIOTIC COMPOSITIONS

This application claims priority to U.S. Provisional application No. 60/569,501, filed May 6, 2004, which is incorporated herein by reference in its entirety.

FIELD OF THE INVENTION

The invention provides compounds and pharmaceutical compositions for the treatment of ocular diseases and disorders, as well as methods of treating such disorders and, more specifically, provides pharmaceutical compositions containing lantibiotics for use in the treatment of ocular diseases and disorders. In particular, pharmaceutical compositions containing duramycin for use in the treatment of ocular diseases and disorders, as well as methods of treatment of ocular diseases using such compositions are provided.

BACKGROUND

Ocular diseases and disorders, including dysfunctions of the eye, eyelids, eyelashes, or lacrimal (tear) system and neuro-opthalmic diseases, affect over three million people per year in the United States alone (Monnet, et al., *Ophthalmology*, 111(4):802-9 (2004)). Many of these cases are difficult to diagnose, and even more difficult to treat. Because the eye in general (especially the cornea) is not vascularized, systemic drugs do not readily permeate it and are generally not used for therapy of ocular diseases or disorders. To date, the topical application of antibiotics has been the preferred treatment, however, the results have been limited results. Consequently, a wide variety of new, alternative compounds have been proposed for use in the treatment of ocular disorders and diseases.

One compound currently used for the treatment of ocular diseases, especially dry eye disease, is the immunomodulator Cyclosporin A. Cyclosporin A (CsA), a fungal-derived immunosuppressive agent, has shown initial promise for the treatment of dry eye/chronic dry eye disease (CDED) (in dogs), severe uveitis, vernal conjunctivitis and to prevent corneal graft rejection in humans; see, for example, Nussenblatt et al., *Survey of Ophthalmology*, 31 (November-December 1986); and BenEzra et al., *American Journal of Ophthalmology*, 101: p. 298 (1986). Most recently, cyclosporin A (RESTASIS™, cyclosporin ophthalmic emulsion, 0.05%) has received FDA approval for use in increasing the tear production in patients whose tear production is presumed to be suppressed due to ocular inflammation associated with keratoconjunctivitis sicca (chronic dry eye).

While cyclosporin A (CsA) has been shown to be effective initially, formulations containing this compound reported significant side effects, including ocular burning, kidney damage and predilection for tumor formation. This suggests that long term therapeutic use, which is usually necessary in the case of ocular diseases and disorders, may present a risk. In addition, due to its size and structure, CsA is not water soluble (Merck Index, 13$^{th}$ Ed, no. 2781) and currently must be delivered in a lipophilic formulation which is not optimal for topical ophthalmic use. Further, it often requires several weeks of RESTASIS™ treatment (one drop twice a day) to produce a clinical therapeutic effect and it may take up to 6 months for maximum improvement. Consequently, RESTASIS™ may only sometimes be considered to be an appropriate drug for immediate relief of an uncomfortable irritated eye, or other ocular conditions.

Among the available treatment options for immediate relief of optical disorders such as dry eye disease, topical corticosteroids (e.g., LOTEMAX (Loteprednol Etabonate; Bausch & Lomb), FML or VEXOL 1% (rimexolone ophthalmic suspension; Alcon, Inc.) have the most rapid onset of action. They may be used for the short-term (2 to 4 weeks). However, the use of steroids in the treatment of ocular diseases and disorders is not without problems, as long-term use of steroid eyedrops can cause a rise in eye pressure (perhaps even glaucoma) and development of a cataract. Therefore, compounds which are devoid of these steroid-related side effects are being sought for use as long-term anti-inflammatory agents.

One such agent is BIOTEARS (Biosyntryx), a twice-daily oral nutraceutical formulation available in very small gel caps and designed to enhance the body's ability to absorb and convert Omega 6 fatty acids to a tear-specific series $E_1$ prostaglandins, which have anti-inflammatory properties that alleviate the signs and symptoms of dry eyes. BIOTEARS also contains the iron binding protein lactoferrin, which reportedly helps to inhibit mild viral and bacterial eye infections that cause discomfort for a large number of contact lens wearers.

U.S. Pat. No. 6,565,861 describes formulations for application to mammalian eyes which contain a lipid binding protein (a tear-specific prealbumin, such as lysozyme, lactoferrin, 1 gA, and β-lactoglobulin) and a polar lipid (such as phospholipids and glycolipids), present as a soluble complex in an aqueous electrolyte. The formulations described have shear-thinning and surface tension properties to natural tears and are therefore reportedly useful as artificial tear substitutes for the treatment of dry eyes (e.g. keratoconjunctivitis sicca) as well as in ophthalmic applications in general.

The immunomodulating drug tacrolimus (PROGRAF, previously known as FK-506; Fujisawa USA), often used as a medication for the prophylaxis of rejection in liver transplants and recently approved by the FDA for use as an immunosuppressive for the prevention of organ rejection in kidney transplant recipients, has been reported to have utility as an immunomodulating drug when applied topically in the treatment of a variety of dermatoses. U.S. Pat. No. 6,489,335 (issued Dec. 3, 2002) suggests the non-systemic use of tacrolimus in the treatment of ocular diseases, including dry eye disease, uveitis, scleritis, neuritis, and papilits. However, the reported side effects associated with the use of this compound--including tremors, hypertension, hypophosphatemia, creatinine increase, headache, and diarrhea--suggest that the use of this compound is less than optimal for the treatment of ocular disorders.

U.S. Pat. No. 6,569,903 describes an adrenergic β-receptor agonist having a high selectivity toward an adrenergic $β_2$ receptor, usable as preventives or therapeutics for xerophthalmic disorders and keratoconjunctival disorders. The adrenergic b-receptor agonists described that are reportedly suitable for use include clenbuterol, fenoterol, salbutamol, salmeterol, hexoprenaline, pirbuterol, mabuterol, bambuterol, formoterol, meluadrine, tulobuterol, levosalbutamol, as well as salts of these compounds.

Steroids and antimetabolite compounds, such as cyclophosphamide, have been used orally to treat severe uveitis, such as that associated with Behcet's disease. Oral steroid therapy is usually accompanied by the topical use of steroid therapy (ocular) to more rapidly control the inflammation. Steroids are also typically used in conjunction with antiviral, antiparasitic or antifungal agents to treat uveitis associated with microbial infections. Both antimetabolite and steroid therapies are general immunosuppressive treatments with both ocular and systemic side effects. Development of central serous chorioretinopathy (CSC) following the administration of corticosteroids by diverse routes is a well-known fact (Bowie, E. M., et al., *Arch. Ophthalmo.*, 122 (2): pp. 281-283 (2004); De Nus, E., et al., *Bul. Soc. Belge Ophtalmol.*, 289: pp. 35-41 (2003)). Further, acute visual loss after the use of systemic corticosteroids in patients with long-standing ocular inflammatory disorders in whom CSC could initially be misinterpreted as a worsening of the primary inflammatory condition has recently been reported (Schalenbourg A, Leys A, De Courten C, Coutteel C, Herbort C P., "Corticosteroid-induced central serous chorioretinopathy in patients with ocular inflammatory disorders", *Klinische Monatsblätter für Augenheilkunde*, 219(4): pp. 264-7 (2002)), further supporting the search for compounds useful in the treatment of ocular diseases and disorders while simultaneously minimizing the ocular and/or systemic side effects associated with the treatment.

Lysostaphin, a protein of approximately 27,000 Daltons, is a bacterial endopeptidase highly lethal to *S. aureus* and *S. epidermidis* that has recently been reported by O'Callaghan (U.S. Pat. No. 6,315,996) to be an effective antibiotic for topical treatment of Staphylococcus corneal infections (keratitis). According to the patent, treatment by lysostaphin was more potent than any of the smaller antibiotics that have been previously tested (e.g., tetracyclines, erythromycins, cephalosporins, vancomycin, aminoglycosides, or fluoroquinolones) for use against keratitis. Moreover, topical application of lysostaphin was shown to be effective against some of the highly antibiotic-resistant Staphylococcus strains.

Other approaches to the treatment of ocular disorders, especially dry eye disease, include the administration of nicotinic acetylcholine receptor agonists (see, for example, U.S. Pat. No. 6,277,855; PCT Publication No. WO 0180844A3), the administration of antimicrobial peptides derived from α-melanocyte-stimulating hormone and its equivalents (see, for example, U.S. patent application No. 2004 0033955), and using uridine triphosphates and related compounds as potential therapeutic treatments (see, for example, U.S. Pat. No. 5,900,407; European Patent Application No. 1003474). Uridine triphosphate and compositions containing this and related dinucleotides have also been described for use in reducing intraocular pressure (see, for example, European Patent Application No. 130 7191 A2), treating retinal degeneration (see, for example, EP 1280536), treating otis media (see, for example, U.S. Pat. No. 6,423,694), affecting cornea epithelium extension (see, for example, Japanese Patent Application No. 2002053492A2), and stimulating the removal of fluid in retinal detachment and retinal edema (see, for example, U.S. Pat. No. 6,596,725).

Based upon the limited success of other chemotherapeutic approaches to ocular diseases to date, there exists a need to develop therapeutics for the treatment of ocular diseases and disorders.

It is an object of the present invention to provide improved methods for the treatment of a variety of ocular diseases and disorders.

It is another object of the present invention to provide compositions and formulations for the treatment of ocular diseases and disorders.

SUMMARY OF THE INVENTION

The present invention provides pharmaceutical compositions containing lantibiotics for the treatment of ocular disorders. It has been discovered that duramycin increases the hydration of ocular membranes and therefore can be useful for the treatment of ocular disorders. The present invention also provides methods for the treatment of ocular disorders by providing an effective amount of a composition containing at least one lantibiotic, such as duramycin, in a pharmaceutically acceptable formulation to a diseased eye.

In one embodiment of the present invention, pharmaceutical compositions and formulations containing at least one lantibiotic as described herein for the treatment of ocular disorders and/or diseases are provided. In a particular, pharmaceutical compositions and formulations containing duramycin for the treatment of ocular disorders and/or diseases are provided. In another embodiment, the compositions and formulations provided herein can be used to relieve the ocular discomfort or irritation associated with ocular diseases and disorders.

In one embodiment, the compositions and formulations described herein can be used to treat allergies, glaucoma, cataract, corneal disease, vitreo-retinal diseases, diseases and disorders of the optic nerve, oculosystemic diseases and disorders, diseases and disorders of the uvea and/or a diabetic eye disease. In one embodiment, the corneal diseases can be selected from but not limited to corneal abrasion, conjunctivitis (pink eye), corneal infections, Fuchs' Dystrophy, Herpes Zoster (shingles), Iridocorneal Endothelial Syndrome, keratoconus, Lattice Dystrophy, Map-Dot-Fingerprint Dystrophy, ocular Herpes, pterygium and/or Stevens-Johnson Syndrome. In another embodiment, the diabetic eye disease can be diabetic retinopathy, cataract and/or glaucoma. In a further embodiment, the vtreo-retinal disease can be diabetic retinopathy, macular degeneration, retinal detachments or tears, macular holes, retinopathy of prematurity, retinoblastoma, uveitis, eye cancer, flashes and floaters and/or retinitis pigmentosa. In another embodiment, the ocular disorder and/or disease can be selected from the group including ocular edema, adenoma, uveitis, scleritis, neuritis, and papilitis. In another embodiment of the present invention, a composition for the treatment of ocular diseases or disorders not including dry eye disease is provided, wherein the composition contains at least one lantibiotic.

In one embodiment of the present invention, a composition for the treatment of ocular diseases and disorders containing at least one lantibiotic is provided, wherein the lantibiotic is a Type A or a Type B lantibiotic. In another embodiment, the composition contains a Type B lantibiotic. In a further embodiment, the Type B lantibiotic can be selected from the group including duramycin, duramycin B, duramycin C, analogs of duramycin, or mixtures thereof. In further embodiment of the present invention, a composition for the treatment of ocular diseases or disorders not including dry eye disease is provided, wherein the composition contains at least one lantibiotic or a pharmaceutically acceptable salt thereof wherein the lantibiotic is a Type A or a Type B lantibiotic. In separate embodiment of the present invention, a composition for the treatment of ocular diseases or disorders not including dry eye disease is provided, wherein the composition contains at least one lantibiotic, wherein the lantibiotic is not duramycin.

In an additional embodiment of the present invention, a composition for the treatment of ocular diseases and disorders is provided, wherein the composition contains a compound of Formula I, (I)

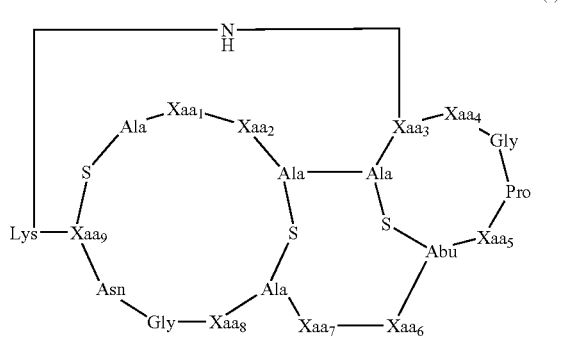

or a pharmaceutically acceptable salt thereof, wherein:

$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

In a separate embodiment of the present invention, a composition for the treatment of ocular diseases and disorders is provided, wherein the composition contains:
(a) a compound of Formula I,

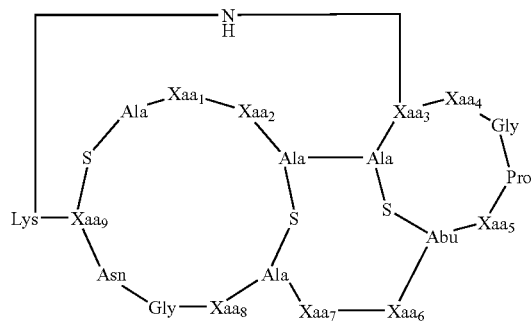

(I)

or a pharmaceutically acceptable salt thereof, wherein
$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine; and
(b) a compound of Formula II,

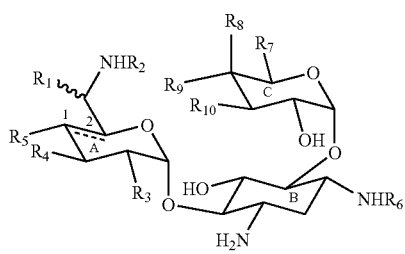

(II)

or a pharmaceutically acceptable salt thereof, wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones.

In yet a further embodiment of the present invention, a composition for the treatment of ocular diseases and disorders is provided, wherein the composition contains:
(a) a compound of Formula I,

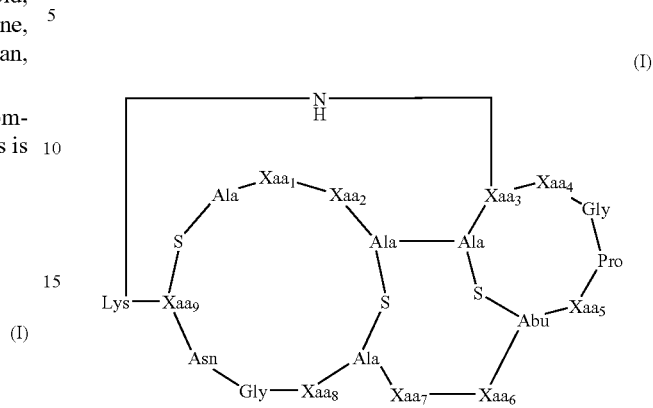

(I)

or a pharmaceutically acceptable salt thereof, wherein
$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine;
(b) a compound of Formula II,

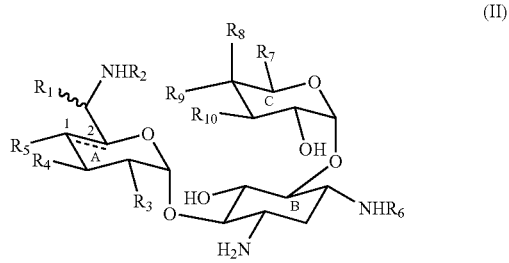

(II)

or a pharmaceutically acceptable salt thereof, wherein
$R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones; and
(c) a therapeutic molecule such as a biologically active protein, wherein the therapeutic molecule is, for example, selected from the group consisting of hormones, antibodies, inhibitors, growth factors, trophic factors, cytokines, lymphokines, toxoids, erythropoietin, Factor VIII, insulin, amylin, TPA, DNases such as domase-α,α-1-antitripsin, human growth hormones, nerve growth hormones, bone morphogenic proteins, urease, toxoids, fertility hormones, FSH, LSH, postridical hormones, tetanus toxoid, diptheria toxoid, vitamins, nutrients, and combinations thereof.

In a further embodiment of the present invention, a composition for the treatment of ocular diseases and disorders containing at least one lantibiotic in combination or alternation with an aminoglycoside is described, wherein the lantibiotic can be a Type B lantibiotic and the aminoglycoside is tobramycin.

In yet another aspect of the present invention, a composition for the treatment of ocular diseases and disorders containing at least one lantibiotic in combination or alternation with an aminoglycoside and a therapeutic protein is described, wherein the lantibiotic is duramycin, the aminoglycoside is preferably tobramycin, and the therapeutic protein is preferably a DNAse.

In an additional embodiment of the present invention, a composition for the treatment of ocular diseases and disorders is described, wherein the ocular disease or disorder is not dry eye disease, and the composition contains a compound of Formula I,

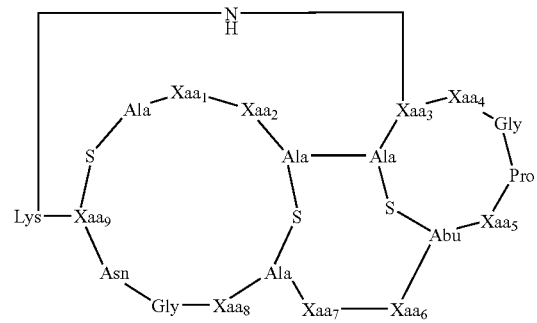

(I)

or a pharmaceutically acceptable salt thereof, wherein:
$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

In a further embodiment of the present invention, a composition for the treatment of ocular diseases and disorders is described, wherein the ocular disease or disorder is not dry eye disease, and the composition contains a compound of Formula I,

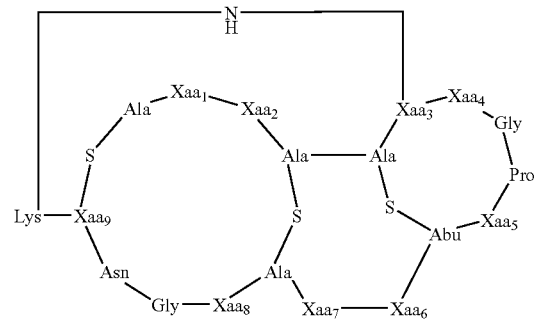

(I)

or a pharmaceutically acceptable salt thereof, wherein:
$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine, wherein the compound of Formula I is not duramycin.

In a further embodiment of the present invention, a composition for the treatment of ocular diseases and disorders is disclosed, wherein the ocular disease or disorder is not dry eye disease and the composition contains:
(a) a compound of Formula I,

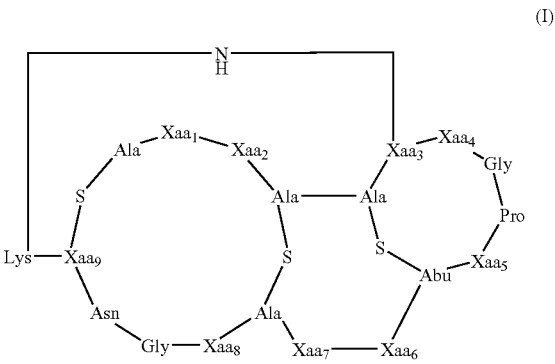

(I)

or a pharmaceutically acceptable salt thereof, wherein is $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine; and
(b) a compound of Formula II,

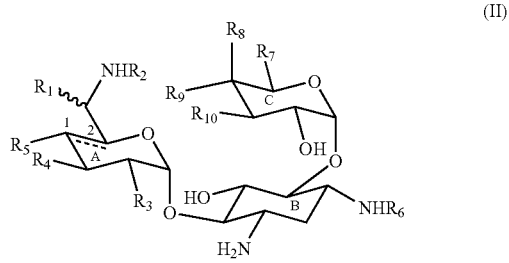

(II)

or a pharmaceutically acceptable salt thereof, wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones.

In a separate embodiment of the present invention, a composition for the treatment of ocular diseases and disorders is disclosed, wherein the ocular disease or disorder is not dry eye disease and the composition contains:
(a) a compound of Formula I,

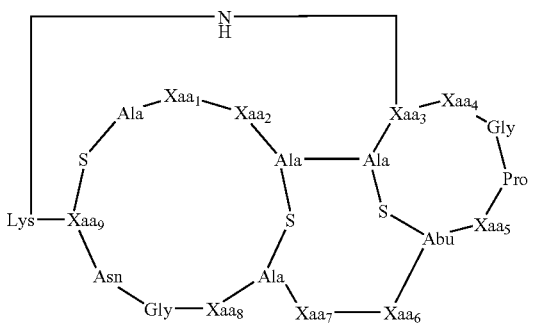

(I)

or a pharmaceutically acceptable salt thereof, wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine, such that the compound of Formula I is not duramycin; and (b) a compound of Formula II,

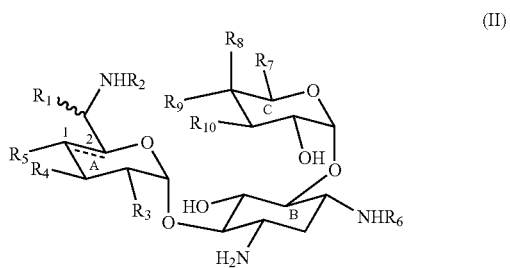

or a pharmaceutically acceptable salt thereof, wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones.

In a further embodiment of the present invention, a method for the treatment of ocular diseases and disorders is described, the method including the administration of a therapeutic amount of a composition containing at least one lantibiotic, wherein the lantibiotic is a Type A lantibiotic, a Type B lantibiotic, or a mixture thereof.

In another embodiment of the present invention, a method for the treatment of ocular diseases and disorders is described, wherein the ocular disease or disorder is not dry eye disease and the method includes the administration of a therapeutic amount of a composition containing at least one lantibiotic, wherein the lantibiotic is a Type A lantibiotic, a Type B lantibiotic, or a mixture thereof.

In an additional embodiment of the present disclosure, a method for the treatment of ocular diseases and disorders is described, the method including administering to a patient a therapeutic amount of a composition containing a composition of Formula I,

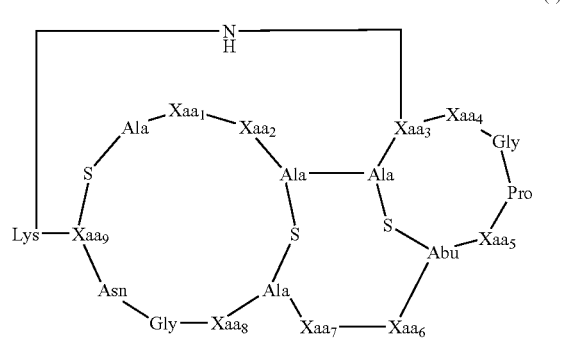

or a pharmaceutically acceptable salt thereof,
wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

In a separate embodiment of the present invention, a method for the treatment of ocular diseases and disorders is described, the method including administering to a patient a therapeutic amount of a composition containing a compound of Formula I

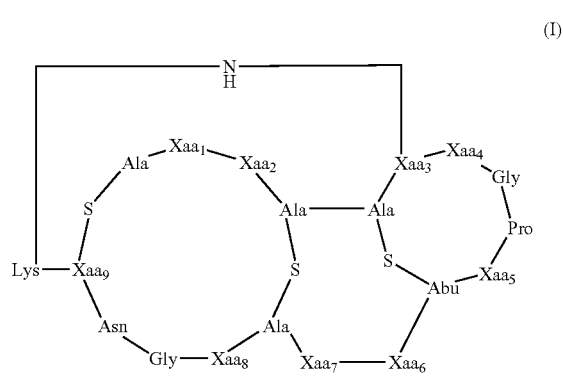

or a pharmaceutically acceptable salt thereof,
wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine; and a compound of Formula II,

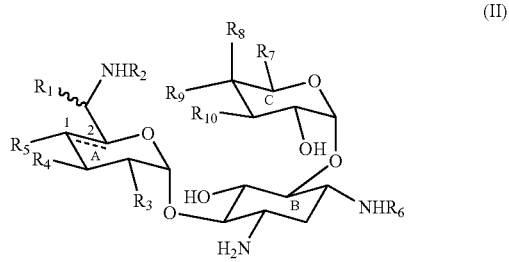

or a pharmaceutically acceptable salt thereof,
wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones.

As a further embodiment of the present disclosure, a method for the treatment of ocular diseases and disorders is described, the method including administering to a patient a therapeutic amount of a composition containing a lantibiotic and an aminoglycoside, wherein the lantibiotic is duramycin and the aminoglycoside is tobramycin.

In a further embodiment of the present invention, a method for the treatment of ocular diseases and disorders is provided, the method including administering to a subject a therapeutic amount of a composition containing a lantibiotic, optionally with one or more other therapeutic agents, wherein the ocular disease or disorder is a disease or disorder other than dry eye disease.

In a further embodiment of the present invention, a method for the treatment of ocular diseases and disorders is provided, the method including administering to a subject a therapeutic amount of a composition containing a lantibiotic that is not duramycin, optionally with one or more other therapeutic agents, wherein the ocular disease or disorder is a disease or disorder other than dry eye.

In one embodiment of the method of the present invention, the ocular disease or disorder is a disease or disorder other than dry eye and optionally the methods do not include the administration of duramycin.

In still another embodiment of the present invention, the use of a composition containing at least one lantibiotic, or a pharmaceutically acceptable salt thereof, for the treatment of an ocular disease or disorder in a subject is described, wherein the composition can optionally include one or more other therapeutic agents.

In a further embodiment of the present invention, the use of a composition containing at least one lantibiotic, or a pharmaceutically acceptable salt thereof, for the treatment of an ocular disease or disorder other than dry eye disease in a subject is described, wherein the composition can optionally include one or more other therapeutic agents.

In yet another embodiment of the present invention, the use of a composition containing at least one lantibiotic, or a pharmaceutically acceptable salt thereof, optionally in combination with one or more other therapeutic agents, in the manufacture of a medicament for the treatment of an ocular disease or disorder, which may optionally not include dry eye disease, in a subject is described.

Further, the present invention provides the following:
a) a pharmaceutical composition for the treatment of an ocular disease or disorder in a subject, containing at least one lantibiotic, or a pharmaceutically acceptable salt thereof, optionally with a pharmaceutically acceptable carrier; and optionally with one or more therapeutic agents;
b) a method for the treatment of an ocular disease or disorder in a subject, including administering an effective amount of a composition containing at least one lantibiotic, or a pharmaceutically acceptable salt thereof, optionally with a pharmaceutically acceptable carrier, excipient, or diluent, and optionally in combination and/or alteration with one ore more other therapeutic agents;
c) use of at least one lantibiotic compound as disclosed herein, or a pharmaceutically acceptable salt thereof, optionally with a pharmaceutically acceptable carrier or diluent, for the treatment of an ocular disease or disorder, optionally in combination with one or more other therapeutic agents; and
d) use of at least one lantibiotic compound as disclosed herein, or a pharmaceutically acceptable salt thereof, optionally in combination with one or more other effective therapeutic agents, and optionally with a pharmaceutically acceptable carrier or diluent, in the manufacture of a medicament for the treatment of an ocular disease or disorder in a subject.

Optionally, in the methods, compositions, and uses disclosed herein, the ocular disease or disorder is a disease or disorder other than dry eye.

DETAILED DESCRIPTION OF THE INVENTION

The present invention provides methods and compositions useful in the treatment of ocular diseases and disorders by the administration of a composition containing at least one lantibiotic. The lantibiotic can be a Type A or Type B lantibiotic, such as duramycin, duramycin B or duramycin C. Additionally, the compositions useful in the present invention for the treatment of ocular diseases and disorders can optionally contain aminoglycosides and/or therapeutic proteins.

While compositions and methods are described in terms of "containing" various components or steps, the compositions and methods can also "consist essentially of" or "consist of" the various components and steps.

I. Ocular Diseases and Disorders

The present invention provides compositions and methods useful in the treatment of ocular diseases and disorders. In another embodiment, the compositions and formulations provided herein can be used to treat ocular diseases or disorders. In another embodiment, the compositions and formulations provided herein can be used to relieve the ocular discomfort or irritation associated with ocular diseases and disorders, such as those diseases and disorders disclosed herein.

In one embodiment, the methods and compositions described herein can be used to treat mammals. A mammal, as a subject or patient in the present disclosure, can be from the family of Primates, Carnivora, Proboscidea, Perissodactyla, Artiodactyla, Rodentia, and Lagomorpha. Among other specific embodiments a mammal of the present invention can be *Canis familiaris* (dog), *Felis catus* (cat), *Elephas maximus* (elephant), *Equus caballus* (horse), *Sus domesticus* (pig), *Camelus dromedarious* (camel), *Cervus axis* (deer), *Giraffa camelopardalis* (giraffe), *Bos taurus* (cattle/cows), *Capra hircus* (goat), *Ovis aries* (sheep), *Mus musculus* (mouse), *Lepus brachyurus* (rabbit), *Mesocricetus auratus* (hamster), *Cavia porcellus* (guinea pig), *Meriones unguiculatus* (gerbil), or *Homo sapiens* (human). In a particular embodiement, the mammal is a human. In other embodiments, animals can be treated, the animals can be vertebrates, including both birds and mammals. Birds suitable as subjects within the confines of the present invention include *Gallus domesticus* (chicken) and *Meleagris gallopavo* (turkey).

Ocular diseases and disorders suitable for treatment by the compositions and formulations of the present disclosure include but are not limited to diseases and disorders of the optic nerve, oculosystemic diseases and disorders, vitreous and retina associated diseases and disorders, diseases and disorders of the cornea, and diseases and disorders of the uvea. Also included as ocular diseases or disorders suitable for treatment with formulations and/or compositions of the present disclosure are disorders such as diabetic retinopathy, where new capillaries in the retina invade the vitreous, bleed and cause blindness, as well as disorders related to the shrinkage, contraction or closing of blood vessels, such as restenosis. Additional ocular diseases or disorders suitable for treatment with compositions of the present invention include cytomegalovirus (CMV) infections, especially those present in immunocompromised subjects such as AIDS patients.

In one embodiment, the compositions and formulations described herein can be used to treat allergies, glaucoma, cataract, corneal disease, vitreo-retinal diseases, and/or a diabetic eye disease. In one embodiment, the corneal diseases can be selected from but not limited to corneal abrasion, conjunctivitis (pink eye), corneal infections, Fuchs' Dystrophy, Herpes Zoster (shingles), Iridocorneal Endothelial Syndrome, keratoconus, Lattice Dystrophy, Map-Dot-Fingerprint Dystrophy, ocular Herpes, pterygium and/or Stevens-Johnson Syndrome. In another embodiment, the diabetic eye disease can be diabetic retinopathy, cataract and/or glaucoma. In a further embodiment, the vtreo-retinal disease can be diabetic retinopathy, macular degeneration, retinal detachments or tears, macular holes, retinopathy of prematurity, retinoblastoma, uveitis, eye cancer, flashes and floaters and/or retinitis pigmentosa. In another embodiment, the ocular disorder and/or disease can be selected from the group including ocular edema, adenoma, uveitis, scleritis, neuritis, and papilitis. In another embodiment of the present invention, a composition for the treatment of ocular diseases or disorders not including dry eye disease is provided, wherein the composition contains at least one lantibiotic.

Specific ocular diseases and disorders which formulations of the present invention are can be used to treat include, but are not limited to: blepharitis; giant papillary conjunctivitis (GPC), "red eye"; pterygium; pinguecula; corneal ulcers; keratoconus; foreign bodies; dry eye syndrome; ocular tumors; neovascularization; cataracts; macular degeneration; diabetic retinopathy; retinal detachment; glaucoma; papillophlebifis; cytomegalovirus (CMV) infection; neuritis; amaurosis fugax; adenoma; systemic lupus erythematosus; neurofibromatosis; Sjögren's syndrome; Behcet's diseases; Keratoconjunctivitis sicca (KCS); Vogt-Koyanagi-Harada disease (Oculocutaneous syndrome, or uveocutaneous syndrome), also known as Harada's disease, Vogt-Koyanagi syndrome, and Yugé's syndrome (see, for example, A. Cowper: *Harada's disease and Vogt-Koyanagi syndrome*. Archives of Ophthalmology, Chicago, 1951, 45: 367-376); antiphospholipid antibody syndrome; ocular cancer; ocular sickling disorders; ocular tuberculosis; giant cell arteritis; myasthenia gravis; sarcoidosis; sickle cell disease; syphilis; albinism; diabetes mellitus; hypertension; edema, including cystoid macular edema; asteroid hyalosis; myopia; staphyloma; toxocariasis (ocular larva migrans); hollenhorstplaque; retinoschisis; choroidal melanoma; retinitis pigmentosa; ocular histoplasmosis syndrome; ocular ischemic syndrome; Terrien's degeneration; acanthamoeba keratitis; fungal keratifis; filamentary keratitis; bacterial keratitis; phylctenulosis; Salmann's Nodular degeneration; pseudoexfoliation syndrome; uveitis, including anterior uveitis; ocular hypertension; hyphema; Axenfeld-Rieger Syndrome; Adie's Pupil, Amaurosis Fugax, Amblyopia, Aphakia, Arcus Senilis, Bell's Palsy, Blepharitis, Chalazion, Conjunctivitis, Corneal Edema, Corneal Erosion, Corneal Ulcer, Central Retinal Artery Occlusion, Central Retinal Vein Occlusion, Central Serous Retinopathy, Dacryocystitis, Dermatochalasis, Diplopia, Drusen, Ectropion, Entropion, Epiretinal Membrane, Esotropia, Exophthalmos, Exotropia, Fuchs' Dystrophy, Hemianopia, Hyphema, Herpes Simplex, Herpes Zoster "shingles", Iritis, Keratitis, Keratoconus, Macular Edema, Neovascularization, Nystagmus, Ocular Migraine, Optic Neuritis, Papilledema, Pinguecula, Pterygium, Ptosis, Retinal Detachment, Rubeosis, Scotoma, Strabismus, Stye, Trichiasis, Uveitis, Vitreous Detachment and pars planitis. Other ocular diseases and disorders are known to those skilled in the art (see for example, Yanoff, M., et al., "Ophthalmology, $2^{nd}$ Ed", Mosby, Inc., 2004).

In another embodiment, the compositions and formulations provided herein can be used treat the ocular disorders and diseases, disclosed below in Table 1 and/or can be used to relieve the ocular discomfort or irritation associated with ocular diseases and disorders, disclosed below in Table 1. Table 1 provides ocular diseases and disorders as well as additional systemic diseases that can cause ocular diseases or discomfort.

TABLE 1

Acanthamoeba Keratitis
Accommodative Esotropia
Acquired Nasolacrimal Duct Obstruction
Acquired Nystagmus
Acute Corneal Hydrops
Acute Retinal Necrosis
Adult Orbital Tumors
Afferent Pupillary Defect
AIDS TABLE 1-continued Albinism
Allergic Conjunctivitis
Allergic Sinusitis
Amaurosis Fugax
Amblyopia
Angle Closure Glaucoma
Angle Recession Glaucoma
Anterior Uveitis
Arteritic Ischemic Optic Neuropathy
Asteroid Hyalosis
Astigmatism
Background Diabetic Retinopathy
Bacterial Conjunctivitis
Bacterial Corneal Ulcer
Basal Cell Carcinoma
Behcet's Disease
Bell's Palsy
Best's Disease
Blepharitis
Blepharospasm
Blind, Painful Eye
Branch Retinal Artery Occlusion
Branch Retinal Vein Occlusion
Bullous Keraathy
Capillary Hemangioma
Cataract
Cavernous Hemangioma
Cellulitis
Central Retinal Artery Occlusion
Central Retinal Vein Occlusion
Central Serous Choroidopathy
Chalazion
Chemical Burn
Childhood Orbital Tumors
Choroidal Detachment
Choroidal Malignant Melanoma
Choroidal Neovascular Membrane
Choroideremia
Chronic Open Angle Glaucoma
Cicatricial Pemphigoid
Clinically Significant Macular Edema
CMV Retinitis
Coat's Disease
Cogan-Reese Syndrome
Color Blindness
Commotio Retinae
Congenital Cataract
Congenital Glaucoma
Congenital Hereditary Endothelial Dystrophy
Congenital Hypertrophy of the Retinal Pigment Epithelium
Congenital Nasolacrimal Duct Obstruction
Congenital Nystagmus
Congenital Ptosis
Conjunctival Hemorrhage
Conjunctival Malignant Melanoma
Conjunctivitis
Contact Lens Related Problems
Contact Lens Solution Hypersensitivity
Convergence Insufficiency
Corneal Abrasion
Corneal Edema
Corneal Foreign Body
Corneal Ulcer
Cranial Nerve Palsy
Cystoid Macular Edema
Dacryocystitis
Dermatochalasis
Dermoid and Epidermoid Cysts
Diabetic Retinopathy
Diffuse Scleritis
Dislocated Intraocular Lens
Distorted Vision
Double vision
Dry Macular Degeneration
Duane's Syndrome
Ectropion TABLE 1-continued Endophthalmitis
Entropion
Epiretinal Membrane
Episcleritis
Esotropia
Exotropia
Exposure Keratitis
Exudative Retinal Detachment
Flashes of Light
Floaters
Fourth Cranial Nerve Palsy
Fuch's Endothelial Dystroph
Fungal Corneal Ulcer
Gardner Syndrome
Giant Papillary Conjunctivitis
Glaucoma
Grave's Disease
Gyrate Atrophy
Halos
Herpes Simplex Virus
Herpes Zoster Virus
Hordeolum
Horner's Syndrome
Hyperopia
Hypertensive Retinopathy
Hypertropia
Hyphema
Hypotony
Infectious Sinusitis
Inflammatory Pseudotumor
Intraocular Foreign Body
Involutional Ptosis
Iris Malignant Melanoma
Irregular Astigmatism
Ischemic Optic Neuropathy
Juvenile Rheumatoid Arthritis
Juvenile Xanthogranuloma
Kaposi's Sarcoma
Kearns-Sayre Syndrome
Keratoconus
Leber's Congenital Amaurosis
Leber's Hereditary Optic Neuropathy
Leukocoria
Low-Tension Glaucoma Lymphoid Tumor
Macular Degeneration
Macular Hole
Map Dot Fingerprint Dystrophy
Marfan's Syndrome
Melanoma
Metastatic Neuroblastoma
Metastatic Orbital Tumors
Migraine
Multiple Sclerosis
Myasthenia Gravis
Myopia
Nasolacrimal Duct Obstruction
Necrotizing Scleritis
Neovascular Glaucoma
Neurofibroma
Neurofibromatosis
Night Blindness
Nodular Scleritis
Non-Arteritic Ischemic Optic Neuropathy
Nystagmus
Ocular Cicatricial Pemphigoid
Ocular Hislasmosis Syndrome
Ocular Rosacea
Optic Nerve Glioma
Optic Nerve Sheath Meningioma
Optic Neuritis
Orbital Blowout Fracture
Orbital Cellulitis
Orbital Inflammatory Pseudotumor
Orbital Lymphoid Tumor
Painful Eye
Papilledema
Pars Planitis
Peripheral Vision Loss TABLE 1-continued Persistent Hyperplastic Primary Vitreous (PHPV)
Peter's Anomaly
Phlyctenulosis
Pigmentary Glaucoma
Pingueculum
Pituitary Tumor
Plaquenil Toxicity
Posner-Schlossman Syndrome
Posterior Capsular Opacity
Posterior Scleritis
Posterior Uveitis
Posterior Vitreous Detachment
Pregnancy
Presbyopia
Preseptal Cellulitis
Primary Open Angle Glaucoma
Prism
Proliferative Diabetic Retinopathy
Proptosis
Pseudoesotropia
Pseudoexfoliative Glaucoma
Pseudotumor Cerebri
Pseudoxanthoma Elasticum
Pterygium
Ptosis
Recurrent Corneal Erosion
Red Eye
Refractive Error
Reiter's Syndrome
Retinal Detachment
Retinal Migraine
Retinitis Pigmentosa
Retinoblastoma
Retinopathy of Prematurity
Retinoschisis
Rhabdomyosarcoma
Rhegmatogenous Retinal Detachment
Rieger's Anomaly/Syndrome
Sarcoidosis
Scleritis
Sinusitis
Sixth Nerve Palsy
Skin Malignant Melanoma
Spasmus Nutans
Squamous Cell Carcinoma
Stargardt's Disease
Steroid Induced Glaucoma
Stevens-Johnson Syndrome
Strabismus
Stroke
Superior Limbic Keratoconjunctivitis
Swollen Eyelid
Sympathetic Ophthalmia
Syphilis
Tearing
Temporal Arteritis
Third Nerve Palsy
Tight Contact Lens Syndrome
Toxocariasis
Toxoplasmosis
Trachoma
Tractional Retinal Detachment
Trichiasis
Ultraviolet Keraathy
Uveitis
Vernal Keratoconjunctivitis
Viral Conjunctivitis
Vision Abnormalities
Visual Migraine
Vitreous Hemorrhage
Vogt-Koyanagi-Harada Syndrome
Wilson's Disease
Wet Macular Degeneration In the embodiments disclosed herein, it is recognized that the methods, compounds, compositions and formulations can be used to treat ocular diseases and disorders, wherein the ocular disease is not dry eye or a related syndrome. In other embodiments, the methods, compounds, compositions and formulations provided herein do not treat the following types of dry eye disease: keratoconjunctivitis sicca (KCS), age-related dry eye, Stevens-Johnson syndrome, Sjogren's syndrome, ocular cicatrical pemphigoid, blepharitis, Riley-Day syndrome, and congenital alacrima or causes of dry eye disease such as nutritional disorders or deficiencies (including vitamins), pharmacologic side effects, eye stress and glandular and tissue destruction, environmental exposure to smog, smoke, excessively dry air, airborne particulates, autoimmune and other immunodeficient disorders, and comatose patients who are unable to blink, such as described in WO 04/037167.

II. Compounds

Duramycin is a polypeptide lantibiotic, characterized by the presence of rings formed by two unusual double-headed amino acid that contain thioether bridges, which enhances chloride secretion in airway epithelium and has been used in studies of cystic fibrosis (CF) (see, Cloutier, M. M., et al., *Am. J. Physiol.* 259, C450 (1990); Nakamura, S.; Racker, E., *Biochemistry* 23, 385 (1984); Twomey, D., et al., *Antonie van Leeuwenhoek* 82: 165-185 (2002)). Duramycin has also been shown to inhibit clatharin-coated vesicle acidification, inhibiting up to 50% of the proton translocation facilitated by chloride translocation (Stone, D. K., et al., *J. Biol. Chem.* 259: 2701-2703 (1984)).

U.S. Publication No. 2004/0147440 to Thorpe et al. describes the use of duramycin as a cell targeting molecule and teach the attachment of therapeutic molecules to the duramycin for tumor vascular targeting, imaging and treatment. Thorpe et al. take advantage of the ability of duramycin to bind to phosphatidylethanolamine, which allows it to act as a tumor targeting agent.

Lantibiotics such as duramycin have also been shown to facilitate the clearance of retained pulmonary secretions from the lungs. U.S. Pat. Nos. 5,512,269; 5,651,957; 5,683,675; and 5,716,931 to Molichem Medicines, Inc. describe methods of administering lantiobiotics, such as duramycin, to the lungs of a subject to treat cystic fibrosis, chronic bronchitis, asthma and tuberculosis.

Recently, Molina et al. discovered that lantibiotics can be used in the treatment of dry eye disease. PCT publication No. WO 2004/037167 to Molichem Medicines, Inc., published May 6, 2004, describes methods for the treatment of dry eye disease, such as keratoconjunctivitus, with a lantibiotic, such as duramycin (as shown in Example 2 of that publication).

Lantibiotics are antibiotic peptides distinguished by the presence of the rare thioether amino acids lanthionine and/or methyllanthionine. They are produced by Gram-positive bacteria as gene-encoded precursor peptides and undergo post-translational modification to generate the mature peptide. The structural gene for the prepeptide and the genes involved in biosynthesis, processing, export as well as regulation and producer strain self-protection are organized in clusters. Based on their structural and functional features lantibiotics are currently divided into two major groups—type A and type B lantibiotics. The flexible amphiphilic type-A lantibiotics act primarily by pore formation in the bacterial membrane, a mechanism which was recently shown, e.g. for nisin and epidermin, to involve the interaction with specific docking molecules such as the membrane precursor lipid II. The rather rigid and globular type-B lantibiotics inhibit enzyme functions through interaction with the respective substrates: mersacidin and actagardine inhibit the cell wall biosynthesis by complexing lipid II, whereas the cinnamycin-like peptides inhibit phospholipases by binding phosphoethanolamine (Hoffinan, A., et al., *Il Farmaco*, 57: pp. 685-691 (2001); Pag, U., et al., *Current Pharm. Design*, 8: pp. 815-833 (2002)).

Lantibiotics are defined as bacterium-derived ribosomally synthesized lanthionine-containing peptides with antibiotic activity (Jack, et al., 1995, *Microbiol. Rev.* 59:171-200; Bierbaum et al., 1993, *Zentralbl. Bakteriol.* 278:1-22; Jack, et al., 1995, *Trends Biotechnol.* 13:269-278). They generally contain unsaturated amino acids like 2,3-didehydroalanine (dhA or U) (2)-2,3-didehydrobutyrine (dhB or O), and 2-aminobutyric acid (Abu). The lantibiotics are divided into two types—Type A and Type B (Jung, 1991, in: Nisin and Novel Lantibiotics., Jung, et al., eds., pp. 1-34. ESCOM Science, Leiden). A further subtype, Type C lantibiotics (the so-called LanC proteins), has also been more recently classified based on more detailed understandings of the previous two classifications (Kupke, T., et al., J Bacteriol., 178: pp. 1335-1340 (1996)). Type A contains screw-shaped, amphipathic molecules with molecular masses between 2151 and 4635 Da and with 2 to 7 net positive charges. Type B consists of more globular molecules with molecular masses between 1825 and 2042 Da and with either no net charge or a net negative charge. They usually contain a higher proportion of modified amino acid residues than type A.

Lantibiotics suitable for use with the present invention include type A, type B and type C lantibiotics, as well as synthetic and natural analogues thereof, and combinations of such lantibiotics. Type A lantibiotics suitable for use with the present invention include but are not limited to nisin, subtilin, epidermin, gallidermin, Pep5, mersacidin, actagardine, and combinations thereof. Type B lantibiotics suitable for use with the present invention include but are not limited to anocovenin, cinnamycin (also known as Ro 09-0198 and lanthiopeptin), duramycin (McNulty, et al., *Xenobiotica*, 33, pp. 197-210 (2003)), also known as leucopeptin, duramycin B, duramycin C, synthetic analogues thereof, and mixtures thereof. In particular, the lantibiotic can be a Type B lantibiotic, or structural analogue of a Type B lantibiotic. More preferably, the lantibiotic suitable for use with the present invention can be a lantibiotic of Formula I,

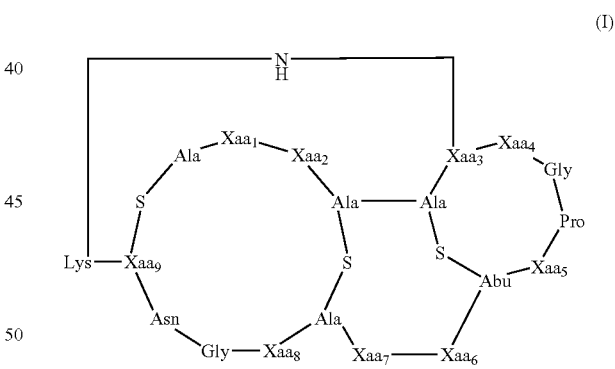

(I)

wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from the group of amino acids (both naturally occurring and synthetic) consisting of but not limited to 2-aminoadipic acid (Aad), aminobutyric acid (Abu), aminobenzoic acid (Abz), aminocyclohexanoic acid (Ac6c), aminocyclopentanoic acid (Ac5c), aminocyclopropanoic acid (Ac3c), aminodecanoic acid (Adc), aminododecanoic acid (Ado), aminohexanoic acid (Ahx), aminoisobutyric acid (Aib), alanine (Ala), alloisoleucine (AIle), allothreonine (aThr), aminomethylbenzoic acid (Amb), aminomethylcyclohexanoic acid (Amc), 2-amino-2-thiazolidine-4-carboxylic acid, aminononanoic acid, aminooctanoic acid, aminopentanoic acid (Avl), arginine (Arg), asparagine (Asn), aspartic acid (Asp), aminoundecanoic acid, aminovaleric acid, biphenylalanine, benzoylphenylalanine, carnitine, 4-cyano-2-aminobutyric acid, 3-cyano-2-aminopropionic acid, cyclohexylalanine, cyclohexylglycine, citruline (Cit), cysteine (Cys), cystine, 2,4-diaminobutyric acid (A2bu), 2,3-diaminopropionic acid (A2pr), diethylglycine, dihydrotryptophan, diaminobenzoic acid, dipropylglycine, 2,3-diaminopropionic acid, 2,3-didehydroalanine (Dha), (Z)-2,3-didehydroaminobutyric acid (Dhb), erythro-3-hydroxyaspartic acid (HyAsp), 2-aminobutyric acid (Abu), dolaproine (Dap), dolaisoluine (Dil), dolaisovaline (Dov), Hiv, methyl valine (MeVal), 3-amino-6-octyneoic acid (Doy), dolaphenine (Doe), dolahexanoic acid (Dhex) 2-methyl-3-aminoisocaproic acid (Dml, dolamethylleuine), 2-amino-4-phenylisovaleric acid (Dpv, dolaphenvaline), diethylglycine, dihydrotryptophan, gamma-carboxyglutamic acid, glutamine (Gln), glutamic acid (Glu), glycine (Gly), histidine (His), homoarginine, homocysteine (Hcy), homophenylalanine, homoserine (Hse), homoserinelactone (Hsl), homotyrosine, hydroxylysine (Hyl), hydroxyproline (Hyp), 2-indolinecarboxylic acid, 2-indanylglycine, isoglutamine (iGln), isoleucine (Ile), indoleglycine, isonipecotic acid, isovaline (Iva), leucine (Leu), lysine (Lys), β-mercapto-β,β-cyclopentamethylenepropanoic acid, methionine (Met), methionine S-oxide (Met(O)), muramicacid (Mur), napthylalanine, neuraminicacid (Neu), norleucine (Nle), norvaline (Nva), octahydroindolecarboxylic acid, omithine (Orn), pyridylalanine, penicillamine, pyroglutamic acid, phenylalanine (Phe), phenylglycine, phosphoserine (Ser(P)), pipecolic acid, 4-phosphomethylphenylalanine, propargylglycine, proline (Pro), putrescine, sarcosine (Sar), serine (Ser), statine (Sta), statine analogs, taurine (Tau), thiazolidinecarboxylic acid, tetrahydroisoquinoline-3-carboxylic acid, tert-leucine, threonine (Thr), thyroxine (Thx), tryptophan (Trp), tyrosine (Tyr), 3,5-diiodotyrosine (Tyr(I$_2$)), valine (Val) and AEEA. Abbreviations for amino acids, as used herein, are in accordance with the IUPAC guidelines on nomenclature (Nomenclature and Symbolism for Amino Acids and Peptides. *Eur. J. Biochem.* 138:9-37(1984)).

Preferably, Xaa$_1$-Xaa$_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine. The lantibiotics used in the compositions of the present invention can be selected from the group consisting of duramycin, duramycin B, duramycin C, structural analogs of duramycin, or a combination thereof. In particular, the lantibiotic is duramycin.

The lantibiotics suitable for use with the present invention can be obtained by isolation from naturally occurring bacterium using known techniques such as fermentation, obtained from commercial sources, produced by genetic engineering techniques, or synthesized using known synthetic chemistry techniques.

In the event that the lantibiotic or lantibiotics of the present invention are prepared by synthetic routes, the amino acids used within the present invention can be obtained from a commercial source (e.g., Advanced ChemTech, Inc., Louisville, Ky.; CalBioChem, Calif.; and, Kyowa Hakko Kogyo Co., LTD., Tokyo, Japan), by fermentation methods, or can be prepared synthetically using any number of techniques in the art, e.g. through the displacement reactions on α-halo acids. For pharmaceutical use, the amino acids are preferably prepared synthetically. The amino acids used within the present invention can be of either the L-(levorotatory), D-(dextrorotatory), or R-(racemic) stereochemical series, and are preferably proteinogenic α-amino acids except for glycine, which does not have optic isomers, and/or β-amino acids, which similarly do not have optic iosomers, but do have several points of optical rotation. Similarly, the lantibiotics of the present invention can also be prepared by biomimetic synthesis means, such as those described by Burrage, S., et al. (*Chem. Eur. J.,* 6: pp. 1455-1466 (2000)).

The amino acids containing the lantibiotic compounds of the present invention, especially those represented by the lantibiotics of Formula I, can exist in different stereoisomeric forms by virtue of the presence of one or more asymmetric centers in the compound. The present invention contemplates L-stereoisomeric forms of the compounds, as well as mixtures thereof, including racemic mixtures. Individual stereoisomers may be obtained commercially, or by methods known in the art, such as the separation of stereoisomers in chiral chromatographic columns.

Further, the lantibiotic compounds of the present invention, especially those of Formula I, can exist in unsolvated as well as solvated forms with pharmaceutically-acceptable solvents such as water, ethanol, and the like. In general, solvated forms of the lantibiotic compounds are considered to be equivalent to the unsolvated forms for the purposes of the present invention.

The isolation of lantibiotics from naturally occurring bacterium includes production and isolation from a variety of known producing strains using known procedures, as well as those techniques described, for example, by Hayashi, et al., (*J. Antibiotics,* 43: pp. 1421-1426; (1990)), Pridham, et al. (*Phytopathology,* 46, pp. 575-581 (1956)), Shotwell, et al. (*J. Am. Chem. Soc.,* 80: pp. 3912-3914 (1958)), and Nakamura, et al. (*Biochemistry,* 23: pp. 385-389 (1984)). Synthetic chemistry techniques include combinatorial chemistry, automated techniques, and the like, such as those described by Bodansky (*Principles of Peptide Synthesis,* 2$^{nd}$ Ed., Springer-Verlag, 1993). Genetic engineering techniques include recombinant techniques based on modified Gram-positive and Gram-negative bacteria, such as those techniques described in the Proceedings of the National Academy of Science, USA (Widdick, et al., Vol. 100, no. 7, pp. 4316-4321; (2003)), and by Sahl ("Gene-Encoded Antibiotics Made in Bacteria", in *Antimicrobial Peptides: Symposium No.* 186 by Ciba Foundation Symposium, pp. 27-53;( 1996)).

Synthesis of lantibiotics for use in the present invention can employ nucleic acid sequences isolated from *S. cinnamoneus* which encode for duramycin or fragments thereof. The nucleic acid sequences can encode for preduramycin, produramycin, the preduramycin leader sequence, or fragments thereof. Alternatively peptides encoded by the duramycin gene and vectors and host cells containing the nucleic acid sequences encoding these peptides can be used, which include, preduramycin, produramycin, the preduramycin leader and derivatives thereof. Such peptides can be isolated and/or purified in accordance with known techniques. In particular, one can introduce into a suitable host cell a nucleic acid sequence encoding preduramycin or produramycin, culturing said cell under suitable conditions to produce such peptides, and isolating preduramycin, produramycin or mature duramycin produced by said cell. The host cell can be a gram-positive bacterium, such as from the genus *Bacillus, Streptomyces* or *Streptococcus.* Such techniques and nucleotide sequences are further described in PCT Publication No, WO 04/033706 to Molichem Medicines, Inc.

In accordance with the present invention, lantibiotics suitable for use in the present invention can also be obtained by fermentation of bacteria of a variety of classes. Such suitable bacteria include but are not limited to Lactic acid bacteria, Streptococcal bacteria, Streptoverticillium bacteria, Micrococcal bacteria, Ruminococcal bacteria, *Bacillus* species, Enterococcal bacteria, *Actinoplanes* species of bacteria, and Carnobacteria.

Examples of bacterial strains suitable for use in the fermentation of lantibiotics useful in the present invention include, but are not limited to, *Streptococcus mutans,* salivarius, pyogenes, grisoluteus, and epidermis; *Streptoverticillium cinnamoneum,* ssp. *Azacolutum; micrococcus varians; Bacillus subtilis; Staphylococcus epidermis, Staphylococcus gallinarum, Staphylococcus cohnil,* and *Staphylococcus warneri;* lactobacteria, including *lactobacillus,* such as *lactobacillus plantarum,* and *lactococcus,* such as *lactococcus lactis* spp.; *Actinoplanes liguriae; Enterococcus faecalis; Ruminococcus gnavus;* and *Carnobacterium piscicola.*

According to a further aspect of the present invention, combinations of lantibiotics with other known compounds are provided, for the purpose of treating ocular diseases and/or ocular conditions. For example, it is envisioned that lantibiotics such as duramycin can be combined with aminoglycosides, resulting in improved treatments of ocular diseases or disorders. As a further example, it is envisioned that lantibiotics such as duramycin can be combined with aminoglycosides and/or therapeutic or prophylactic proteins, resulting in compositions useful in the treatment of ocular diseases or disorders.

Aminoglycosides suitable for use with the present invention in preparing compositions and ophthalmic formulations suitable for use in the treatment of ocular diseases and disorders include those bactericidal antbiotics known in the art that are generally classified as protein synthesis inhibitors that interfere with ribosomal function. Suitable aminoglycosides include but are not limited to streptomycin, neomycin, kanamycin, gentamicins such as gentamicin $C_1$, gentamicin $C_2$, and gentamycin $C_{1a}$, tobramycin, amikacin, butirosin and butirosin A, sisomicin, paromomycin, and netilmicin, as well as structurally modified analogues of such aminoglycosides. Aminoglycosides suitable for use with the present invention include those of Formula (II),

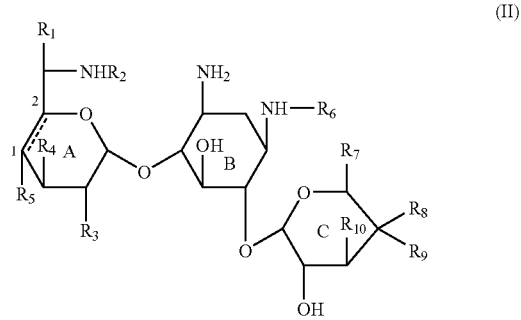

(II)

wherein the dotted line in the chemical structure indicates either a double or single bond such that the double bond does not over-extend the valence of the element (i.e. to give pentavalent carbons) and, in the case of a single bond, the valence is completed with hydrogen; and, wherein $R_1, R_2, R_3, R_4, R_5, R_6, R_7, R_8, R_9,$ and $R_{10}$ are independently selected from the group consisting of hydrogen, amines, alcohols, alkyl alcohols, alkyl amines, substituted alkyl amines, and ketones. In one embodiment, $R_1$-$R_{10}$ are independently selected from the group consisting of methyl ($CH_3$), hydrogen (H), hydroxyl (OH), primary amine ($NH_2$), methyl amine (NH—$CH_3$), and methyl alcohol ($CH_2$—OH). In a particular embodiment, $R_1$, $R_2, R_4, R_5, R_6, R_8$ and $R_9$ are hydrogen, $R_3$ and $R_{10}$ are a primary amine ($NH_2$), and $R_7$ is methyl alcohol ($CH_2$—OH), such that the aminoglycoside of Formula II is tobramycin.

Tobramycin [0-3-amino-3-deoxy-α-D-glucopyranosyl-(1→4)- -0-[2,6-diamino-2,3 ,6-trideoxy-α-D-ribo-hexopyranosyl-(1-'6)]-2-deox- y-L-streptamine], is a known antibiotic drug. See, for example, The Merck Index, Twelfth Edition, page 1619. Inhaled tobramycin was recently approved by the FDA in a 300 mg formulation for inhalation. The new product, manufactured by PathoGenesis Corporation, is referred to as TOBI™ and is indicated for cystic fibrosis patients with Pseudomonas aeruginosa. Both TOBI™, as well as NEBCIN® (tobramycin sulfate) and related salts and compounds are suitable for use in formulation of the present invention. Examples of analogs of tobramycin suitable for use in compositions of the present invention have recently been described by Hanessian, S., et al. (Tetrahedron, 59: pp. 983-993 (2003)), all of which (ethers, ether-linked basic moieties, amino-containing sides chains, and guanidine-containing side chains) are envisioned as being suitable for use herein. The concentration of tobramycin in the solution compositions of the present invention can generally be about 50 wt.% or less. In topically administrable ophthalmic compositions, the concentration of tobramycin can be about 30 wt.%.

As a further alternative formulation composition of the present invention, the formulation can contain a lantibiotic or combination of lantibiotics, an aminoglycoside, and a therapeutic or prophylactic protein or other biologically active compound. Such a formulation can contain a lantibiotic of Formula I, an aminoglycoside of Formula II, and a therapeutic or prophylactic protein or other biologically active drug or compound. In particular, a formulation for use in the treatment of ocular diseases and disorders, in accordance with one aspect of the present invention, can be a duramycin lantibiotic, tobramycin, and a therapeutic protein.

Examples of therapeutic or prophylactic proteins and other biologically active drugs or compounds suitable for use in formulations of the present invention include but are not limited to hormones, antibodies, inhibitors, growth factors, trophic factors, cytokines, lymphokines, toxoids, erythropoietin, Factor VIII, insulin, amylin, tPA (tissue plasminogen activator), dornase-α, α-1-antitripsin, human growth hormones, nerve growth hormones, bone morphogenic proteins, urease, toxoids, fertility hormones, FSH (follicle stimulating hormone), LSH (lutropin-choriogonadotropic hormone), postridical hormones, tetanus toxoid, diptheria toxoid, vitamins and nutrients. In particular, the therapeutic or prophylactic protein is domase-α (Pulmozyme®, from Genentech, San Francisco, Calif.), a recombinant human deoxyribonuclease I (rhDNase).

Definitions

The terms "$C_1$-$C_{10}$ alkyl", "$C_2$-$C_{10}$ alkenyl", $C_1$-$C_{10}$ alkoxy, $C_2$-$C_{10}$ alkenoxy, $C_2$-$C_{10}$ alkynyl, and $C_2$-$C_{10}$ alkynoxy are considered to include, independently, each member of the group, such that, for example, $C_1$-$C_{10}$ alkyl includes straight, branched and where appropriate cyclic $C_1$, $C_2, C_3, C_4, C_5, C_6, C_7, C_8, C_9$ and $C_{10}$ alkyl functionalities; $C_2$-$C_{10}$ alkenyl includes straight, branched, and where appropriate cyclic $C_2, C_3, C_4, C_5, C_6, C_7, C_8, C_9$ and $C_{10}$ alkenyl functionalities; $C_1$-$C_{1\text{-}10}$ alkoxy includes straight, branched, and where appropriate cyclic $C_1, C_2, C_3, C_4, C_5, C_6, C_7, C_8, C_9$ and $C_{10}$ alkoxy functionalities; $C_2$-$C_{10}$ alkenoxy includes straight, branched, and where appropriate cyclic $C_2, C_3, C_4, C_5, C_6, C_7, C_8, C_9$ and $C_{10}$ alkenoxy functionalities; $C_2$-$C_{10}$ alkynyl includes straight, branched and where appropriate cyclic $C_1, C_2, C_3, C_4, C_5, C_6, C_7, C_8, C_9$ and $C_{10}$ alkynyl functionalities; and $C_2$-$C_{10}$ alkynoxy includes straight, branched, and where appropriate cyclic $C_2, C_3, C_4, C_5, C_6, C_7, C_8, C_9$ and $C_{10}$ alkynoxy functionalities.

The term "alkyl", alone or in combination, means an acyclic, saturated straight, branched, or cyclic, primary, secondary, or tertiary hydrocarbon, including those containing from 1 to 10 carbon atoms or from 1 to 6 carbon atoms. Said alkyl radicals may be optionally substituted with groups including but not limited to methyl, ethyl, propyl, isopropyl, cyclopropyl, butyl, isobutyl, t-butyl, sec-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, heptyl, octyl; nonyl, decyl, trifluoromethyl and difluoromethyl. Moieties with which the alkyl group can be substituted include, for example, alkyl, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that preferably does not inhibit the pharmacological activity of the compound, either unprotected, or protected as necessary, as known to those skilled in the art, for example, as taught in Greene, et al., *Protective Groups in Organic Synthesis*, John Wiley and Sons, Third Edition, 1999, hereby incorporated by reference.

The term "alkenyl", alone or in combination, means an acyclic, straight, branched, or cyclic, primary, secondary, or tertiary hydrocarbon, including those containing from 2 to 10 carbon atoms or from 2 to 6 carbon atoms, wherein the substituent contains at least one carbon-carbon double bond. These alkenyl radicals may be optionally substituted. Examples of such radicals include but are not limited to are ethylene, methylethylene, and isopropylidene.

The term "alkynyl" means an unsaturated, acyclic hydrocarbon radical, linear or branched, in so much as it contains one or more triple bonds, including such radicals containing about 2 to 10 carbon atoms or having from 2 to 6 carbon atoms. The alkynyl radicals may be optionally substituted. Examples of suitable alkynyl radicals include but are not limited to ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like.

The terms "alkoxy" and "alkoxyalkyl" embrace linear or branched oxy-containing radicals each having alkyl portions of, for example, from one to about ten carbon atoms, including the methoxy, ethoxy, propoxy, and butoxy radicals. The term "alkoxyalkyl" also embraces alkyl radicals having one or more alkoxy radicals attached to the alkyl radical, that is, to form monoalkoxyalkyl and dialkoxyalkyl radicals. Other alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" includes "monoalkylamino" and "dialkylamino" radicals containing one or two alkyl radicals, respectively, attached to an amino radical. The terms "arylamino" denotes "monoarylamino" and "diarylamino" containing one or two aryl radicals, respectively, attached to an amino radical. The term "aralkylamino", embraces aralkyl radicals attached to an amino radical, and denotes "monoaralkylamino" and "diaralkylamino" containing one or two aralkyl radicals, respectively, attached to an amino radical. The term aralkylamino further includes "monoaralkyl monoalkylamino" containing one aralkyl radical and one alkyl radical attached to an amino radical.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "alkylthio" and "arylthio" are defined as —SR, wherein R is alkyl or aryl, respectively.

The term "alkylsulfinyl" is defined as R—SO$_2$, wherein R is alkyl.

The term "alkylsulfonyl" is defined as R—SO$_3$, wherein R is alkyl.

The term "aryl", alone or in combination, includes a carbocyclic aromatic system containing one, two or three rings wherein such rings may be attached together in a pendent manner or may be fused. Examples of aryl groups include phenyl, benzyl, naphthyl, and biphenyl. The "aryl" group can be optionally substituted where possible with one or more of the moieties including but not limited to alkyl, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that preferably does not inhibit the pharmacological activity of the compound, either unprotected, or protected as necessary, as known to those skilled in the art. In addition, adjacent groups on an "aryl" ring may combine to form a 5- to 7-membered saturated or partially unsaturated carbocyclic, aryl, heteroaryl or heterocyclic ring, which in turn may be substituted as above.

The term "halo" includes fluoro, bromo, chloro, and iodo.

The term "heterocyclic" includes nonaromatic cyclic groups that may be partially (e.g., contains at least one double bond) or fully saturated and wherein there is at least one heteroatom, such as oxygen, sulfur, nitrogen, or phosphorus in the ring. Similarly, the term heteroaryl or heteroaromatic, as used herein, refers to an aromatic that includes at least one sulfur, oxygen, nitrogen or phosphorus in the aromatic ring. Nonlimiting examples of heterocylics and heteroaromatics include pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein the heteroaryl or heterocyclic group can be optionally substituted with one or more substituent selected, for example, from the same substituents as set out above for aryl groups. Functional oxygen and nitrogen groups on the heteroaryl group can be protected as necessary or as desired. Suitable protecting groups can include but are not limited to trimethylsilyl (TMS), dimethylhexylsilyl (DMHS), t-butyldimethylsilyl (TBS or TBDMS), and t-butyldiphenylsilyl (TBDPS), trityl (Trt) or substituted trityl, alkyl groups, acyl (Ac) groups such as acetyl and propionyl, methanesulfonyl, and p-toluenelsulfonyl.

The terms "protecting group" or "protected" refers to a substituent that protects various sensitive or reactive groups present, so as to prevent said groups from interfering with a reaction. Such protection may be carried out in a well-known manner as taught by Greene, et al., *Protective Groups in Organic Synthesis,* John Wiley and Sons, Third Edition, 1999 or the like. The protecting group may be removed after the reaction in any manner known by those skilled in the art. Non-limiting examples of protecting groups suitable for use within the present invention include but are not limited to allyl, benzyl (Bn), tertiary-butyl (t-Bu), methoxymethyl (MOM), p-methoxybenzyl (PMB), trimethylsilyl (TMS), dimethylhexylsily (TDS)l, t-butyldimethylsilyl (TBS or TBDMS), and t-butyldiphenylsilyl (TBDPS), tetrahydropyranyl (THP), trityl (Trt) or substituted trityl, alkyl groups, acyl groups such as acetyl (Ac) and propionyl, methanesulfonyl (Ms), and p-toluenesulfonyl (Ts). Such protecting groups can form, for example in the instances of protecting hydroxyl groups on a molecule: ethers such as methyl ethers, substituted methyl ethers, substituted alkyl ethers, benzyl and substituted benzyl ethers, and silyl ethers; and esters such as formate esters, acetate esters, benzoate esters, silyl esters and carbonate esters, as well as sulfonates, and borates.

III. Pharmaceutical Compositions

Pharmaceutical carriers suitable for administration of the compounds provided herein include any such carriers known to those skilled in the art to be suitable for the particular mode of administration. The compounds may be formulated as the sole pharmaceutically active ingredient in the composition or may be combined with other active ingredients.

Compositions comprising the compounds disclosed herein may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

The compositions may conveniently be presented in unit dosage form and may be prepared by conventional pharmaceutical techniques. Such techniques include the step of bringing into association one or more compositions of the present invention and one or more pharmaceutical carriers or excipients. The term "unit dosage form", or alternatively "unit dosage levels" as used herein refers to physically discrete units suitable as unitary dosages for human subjects, each unit containing a predetermined quantity of active material calculated to produce the desired therapeutic effect in association with the required pharmaceutical diluent, carrier, or vehicle. The specifications for the novel unit dosage forms of this invention are dictated by and are directly dependent upon (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accordance with this invention are tablets, capsules, troches, powder packets, wafers, cachets, teaspoonfuls, tablespoonfuls, dropperfuls, ampules, vials, I.V. bags, segregated multiples of any of the foregoing, and other forms as described herein.

The term "unit dosage form", or alternatively "unit dosage levels" as used herein includes, for example, physically discrete units suitable as unitary dosages for human subjects, each unit containing a predetermined quantity of active material calculated to produce the desired therapeutic effect in association with the required pharmaceutical diluent, carrier, or vehicle. The specifications for the novel unit dosage forms of this invention are dictated by and are directly dependent upon (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accordance with this invention are tablets, capsules, troches, powder packets, wafers, cachets, teaspoonfuls, tablespoonfuls, dropperfuls, ampules, vials, I.V. bags, segregated multiples of any of the foregoing, and other forms as described herein.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof may be mixed with one or more suitable pharmaceutical carriers. The compounds may be derivafized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa., 15th Edition, 1975.

Compositions of the present invention suitable for topical administration in the mouth include for example, lozenges, having the ingredients in a flavored basis, usually sucrose and acacia or tragacanth; pastilles, having one or more of the compositions of the present invention in an inert basis such as gelatin and glycerin, or sucrose and acacia; and mouthwashes, having one or more of the compositions of the present invention administered in a suitable liquid carrier.

The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

The compositions of the present invention can be formulated with additional agents, in particular, when used as a topical forumation, for example, as a drop. Examples of such additional components include buffering agents, cleaning agents, wetting agents, sequestering agents, viscosity builders, tonicity agents, nutrient agents, contact lens conditioning agents, antioxidants, pH adjustors, and the like. These additional components can be included in the present compositions in an amount effective to impart or provide the beneficial or desired property to the compositions.

A surfactant component can also be included in the compositions disclosed herein. The surfactant component can be nonionic. Exemplary surfactant components include, but are not limited to, nonionic surfactants, for example, polysorbates (such as POLYSORBATE 80™, TWEEN® 80, 4-(1,1,3,3-tetramethylbutyl) phenol/poly(oxyethylene) polymers (such as the polymer sold under the trademark TYLOXAPOL®, poly(oxyethylene)-poly(oxypropylene) block copolymers, glycolic esters of fatty acids and the like, and mixtures thereof. The surfactant can be selected from poly (oxyethylene)-poly(oxypropylene) block copolymers and mixtures thereof. Such surfactant components may be obtained commercially from the BASF Corporation under the trademark PLURONIC®. Such block copolymers may be generally described as polyoxyethylene/polyoxypropylene condensation polymers terminated in primary hydroxyl groups. The amount of surfactant component, if any, present varies over a wide range depending on a number of factors, for example, the specific surfactant or surfactants being used, the other components in the composition and the like. The amount of surfactant can be in the range of about 0.005% or about 0.01% to about 0.1% or about 0.5% or about 1.0% or about 2.5% (w/v).

Buffering agents can include, but are not limited to, acetate buffers, citrate buffers, phosphate buffers and borate buffers. Acids and bases can be used to adjust the pH of the present compositions as needed. An appropriate buffer system (e.g., sodium phosphate, sodium acetate, sodium citrate, sodium borate or boric acid) can be added to the compositions to prevent pH drift under storage conditions. The particular concentration will vary, depending on the agent employed. In a particular embodiment, the buffer will be chosen to maintain a target pH within the range of pH 6-7.5.

Wetting agents include, but are not limited to, polyvinyl alcohol, polyoxamers, polyvinyl pyrrolidone, hydroxypropyl methyl cellulose and mixtures thereof. Sequestering agents include, but are not limited to, disodium ethylene diamine tetraacetate, alkali metal hexametaphosphate, citric acid, sodium citrate and mixtures thereof.

Tonicity adjustors include, but are not limited to, sodium chloride, potassium chloride, mannitol, dextrose, glycerin, propylene glycol and mixtures thereof. For example, sodium chloride, potassium chloride, magnesium chloride, calcium chloride, dextrose and/or mannitol can be added to the composition to accommodate physiological tonicity. Such an amount of tonicity agent can vary, depending on the particular agent to be added. In general, however, the compositions can have a tonicity agent in an amount sufficient to cause the final composition to have an ophthalmically acceptable osmolality (generally about 150-450 mOsm, preferably 250-350 mOsm).

Viscosity builders include, but are not limited to, hydroxyethyl cellulose, hydroxypropyl methylcellulose, carboxymethyl cellulose, polyvinyl pyrrolidone, polyvinyl alcohol and mixtures thereof. Compounds to enhance the viscosity of the composition include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Antioxidants include, but are not limited to, sodium metabisulfite, sodium thiosulfate, N-acetylcysteine, butylated hydroxyanisole, butylated hydroxytoluene and mixtures thereof. Examples of additional antioxidants include, but are not limited to, vitamin E and analogs thereof, ascorbic acid and derivatives, and butylated hydroxyanisole (BHA).

Preservatives can also be added to the formulations. Preservatives include, but are not limited to: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives can be employed at a level of from 0.001 to 1.0% w/v.

Compositions for rectal administration may be presented as a suppository with a suitable base comprising, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions may be used as the active ingredient in combination with one or more pharmaceutically acceptable carrier mediums and/or excipients. As used herein, "pharmaceutically acceptable carrier" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; drugs used in combination or coincidential with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered ingredient. The dosage will depend on host factors such as weight, age, surface area, metabolism, tissue distribution, absorption rate and excretion rate. Exemplary systemic dosages for all of the herein described conditions are those ranging from 0.1 mg/kg to 500 mg/kg of body weight per day as a single daily dose or divided daily doses. Typical dosages for topical application are those ranging from 0.001 to 100% by weight of the active compound.

The therapeutically effective dose level will depend on many factors as noted above. In addition, it is well within the skill of the art to start doses of the composition at relatively low levels, and increase the dosage until the desired effect is achieved.

Compositions containing a compound disclosed herein may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The compounds may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

Any suitable dosage can be used in the treatment or prevention of membrane-associated diseases or disorders. Non-limiting examples include: dosage levels about 0.01 to 500 mg per kg patient body weight per day which can be administered in single or multiple doses. in particular, the dosage level can be about 0.1 to about 250 mg/kg per day; in one embodiment it is about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions can be provided in the form of tablets containing 1.0 to 1000 milligrams of the active ingredient, and in particular can be 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds can be be administered on a regimen of 1 to 4 times per day, in one embodiment they can be administered once or twice per day.

All of the compositions, methods and/or processes disclosed and claimed herein can be made and executed without undue experimentation in light of the present disclosure. While the compositions and methods of this invention have been described in terms of embodiments, it will be apparent to those of skill in the art that variations can be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A method for relieving the ocular discomfort or irritation associated with an ocular disease or disorder in a mammal comprising administering an effective amount of a lantibiotic to the mammal, wherein the ocular disease or disorder is selected from the group consisting of allergies, glaucoma, cataract, corneal disease, vitreo-retinal diseases, diseases and disorders of the optic nerve, oculosystemic diseases and disorders, diseases and disorders of the uvea and/or a diabetic eye disease.

2. The method of claim 1, wherein the lantibiotic is the compound of Formula I:

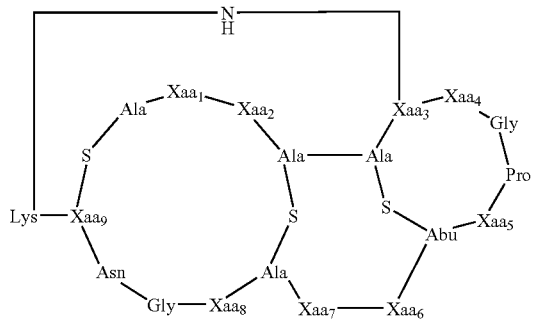

or a pharmaceutically acceptable salt thereof, wherein:
Xaa$_1$, Xaa$_2$, Xaa$_3$, Xaa$_4$, Xaa$_5$, Xaa$_6$, Xaa$_7$, Xaa$_8$, and Xaa$_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

3. The method of claim 1, wherein the lantibiotic is a Type A or Type B lantibiotic.

4. The method of claim 3, wherein the lantibiotic is a Type B lantibiotic.

5. The method of claim 4, wherein the Type B lantibiotic is duramycin.

6. The method of claim 1, wherein the lantibiotic is administered in combination or alternation with an aminoglycoside.

7. The method of claim 6, wherein the aminoglycoside is tobramycin.

8. The method of claim 1, wherein the corneal disease is selected from the group consisting of corneal abrasion, conjunctivitis, corneal infections, Fuchs' Dystrophy, Herpes Zoster (shingles), Iridocorneal Endothelial Syndrome, keratoconus, Lattice Dystrophy, Map-Dot-Fingerprint Dystrophy, ocular Herpes, pterygium and Stevens-Johnson Syndrome.

9. The method of claim 1, wherein the diabetic disease is a diabetic retinopathy, cataract or glaucoma.

10. The method of claim 1, wherein the viteo-retinal disease is selected from the group consisting of diabetic retinopathy, macular degeneration, retinal detachment, macular holes, retinopathy of prematurity, retinoblastoma, uveitis, eye cancer, flashes, floaters and retinitis pigmentosa.

* * * * *